(12) United States Patent
Nakajima

(10) Patent No.: US 7,935,795 B2
(45) Date of Patent: May 3, 2011

(54) HUMAN MONOCLONAL ANTIBODY BINDING TO HGM-CSF AND ITS ANTIGEN BINDING PORTION

(75) Inventor: Kantou Nakajima, Sapporo (JP)

(73) Assignee: Evec Inc., Sapporo (JP)

( * ) Notice: Subject to any disclaimer, the term of this patent is extended or adjusted under 35 U.S.C. 154(b) by 0 days.

(21) Appl. No.: 12/149,009

(22) Filed: Apr. 24, 2008

(65) Prior Publication Data

US 2008/0317757 A1     Dec. 25, 2008

Related U.S. Application Data

(63) Continuation-in-part of application No. PCT/JP2006/320502, filed on Oct. 13, 2006.

(30) Foreign Application Priority Data

Oct. 26, 2005 (JP) ................................ 2005-311776

(51) Int. Cl.
*C12P 21/08* (2006.01)
(52) U.S. Cl. ........... 530/388.23; 530/388.15; 530/388.1; 530/387.1
(58) Field of Classification Search ........................ None
See application file for complete search history.

(56) References Cited

U.S. PATENT DOCUMENTS

| | | | | |
|---|---|---|---|---|
| 5,662,138 | A * | 9/1997 | Wang | 137/433 |
| 7,084,257 | B2 * | 8/2006 | Deshpande et al. | 530/387.9 |
| 7,138,501 | B2 * | 11/2006 | Ruben et al. | 530/388.23 |
| 7,193,069 | B2 * | 3/2007 | Isogai et al. | 536/23.1 |
| 7,229,784 | B2 * | 6/2007 | Holtzman et al. | 435/41 |
| 7,282,205 | B2 * | 10/2007 | Schofield et al. | 424/141.1 |
| 7,326,414 | B2 * | 2/2008 | Bedian et al. | 424/141.1 |
| 7,361,740 | B2 * | 4/2008 | Hinton et al. | 530/387.3 |
| 2003/0103968 | A1 | 6/2003 | Amelsberg et al. | |
| 2010/0010202 | A1 | 1/2010 | Kucherlapati et al. | |

FOREIGN PATENT DOCUMENTS

| | | |
|---|---|---|
| EP | 0 265 384 A2 | 4/1988 |
| EP | 0 499 161 A2 | 8/1992 |
| JP | 05-176792 | 7/1993 |
| WO | WO 03/068924 A2 | 8/2003 |
| WO | WO 2005/105844 A2 | 11/2005 |
| WO | WO 2006/111353 A2 | 10/2006 |
| WO | WO 2006/122797 A2 | 11/2006 |
| WO | WO 2007/049472 A1 | 5/2007 |
| WO | WO 2007/092939 A2 | 9/2007 |

OTHER PUBLICATIONS

Paul, Fundamental Immunology, 3r~ Edition, 1993, pp. 292-295, under the heading "Fv Structure and Diversity in Three Dimensions".*
Rudikoff et al Proc. Natl. Acad. Sci.USA, 79(6):1979-1983, Mar. 1982.*
Colman P. M. Research in Immunology, 145:33-36, 1994.*
Goodman and Gilman, 10th edition, McGraw-Hill, 2001, p. 3-29.*
Bozinovski et al., "Innate immune responses to LPS in mouse lung are suppressed and reversed by neutralization of GM-CSF via repression of TLR-4," *Amer J Physiol Lung Cell Mol Physiol* 286(4):L877-L885 (2004).
Fleetwood et al., "Functions of granulocyte-macrophage colony-stimulating factor," *Crit Rev Immunol* 25(5):405-428 (2005).
Green, L.L., "Antibody engineering via genetic engineering of the mouse: XenoMouse strains are a vehicle for the facile generation of therapeutic human monoclonal antibodies," *J Immunol Meth* 231(1-2):11-23 (1999).
Griffiths et al., "Strategies for selection of antibodies by phage display," *Curr Opin Biotech* 9(1):102-108 (1998).
Hamilton, J.A., "GM-CSF in inflammation and autoimmunity," *Trends Immunol* 23(8):403-408 (2002).
Hoogenboom, H.R., "Designing and optimizing library selection strategies for generating high-affinity antibodies," *Trends Biotech* 15(2):62-70 (1997).
Rathanaswami et al., "Demonstration of an in vivo generated sub-picomolar affinity fully human monoclonal antibody to interleukin-8," *Biochem Biophys Res Comm* 334(4):1004-1013 (2005).
Schön et al., "Critical role of neutrophils for the generation of psoriasiform skin lesions in flaky skin mice," *J Invest Dermatology* 114(5):976-983 (2000).
Yamashita et al., "Attenuation of airway hyperresponsiveness in a murine asthma model by neutralization of granulocyte-macrophage colony-stimulating factor (GM-CSF)," *Cell Immunol* 219(2):92-97 (2002).
D L Bratton, Q Hamid, M Boguniewicz, D E Doherty, J M Kailey, and D Y Leung "Granulocyte macrophage colony-stimulating factor contributes to enhanced monocyte survival in chronic atopic dermatitis" J Clin Invest.; 95(1): 211-218, Jan. 1995. Elizabeth C. Cates, Ramzi Fattouh, Jennifer Wattie, Mark D. Inman, Susanna Goncharova, Anthony J. Coyle, José-Carlos Gutierrez-Ramos and Manel Jordana Intranasal Exposure of Mice to House Dust Mite Elicits Allergic Airway Inflammation via a GM-CSF-Mediated Mechanism The Journal of Immunology, 173: pp. 6384-6392, 2004.
Ohta K, Yamashita N, Tajima M, Miyasaka T, Nakano J, Nakajima M, Ishii A, Horiuchi T, Mano K, Miyamoto T. "Diesel exhaust particulate induces airway hyperresponsiveness in a murine model: essential role of GM-CSF" J Allergy Clin Immunol.;104(5): pp. 1024-1030, Nov. 1999.

(Continued)

*Primary Examiner* — Shulamith H Shafer
(74) *Attorney, Agent, or Firm* — Wolf, Greenfield & Sacks, P.C.

(57) ABSTRACT

The present invention provides a human monoclonal antibody, and antigen-binding portions thereof, capable of binding to human granulocyte-macrophage colony stimulating factor (hGM-CSF) and neutralizing the bioactivity of the hGM-CSF, wherein the anti-hGM-CSF monoclonal antibody has a light chain (L chain) including an amino acid sequence SEQ ID NO:1 and a heavy chain (H chain) including an amino acid sequence SEQ ID NO: 2. Also provided are human monoclonal anti-hGM-CSF antibodies, and antigen-binding portions thereof, characterized by complementarity determining regions (CDRs) or H chain and L chain variable regions related to SEQ ID NO:1 and SEQ ID NO:2. Antibodies, and antigen-binding portions thereof, of the invention are useful in the treatment of diseases associated with overproduction of hGM-CSF, including allergic disease, graft rejection and graft-versus-host disease (GVHD), and autoimmune diseases.

18 Claims, 7 Drawing Sheets

OTHER PUBLICATIONS

R J Bischof, D Zafiropoulos, J A Hamilton, and I K Campbell "Exacerbation of acute inflammatory arthritis by the colony-stimulating factors CSF-1 and granulocyte macrophage (GM)-CSF: evidence of macrophage infiltration and local proliferation" Clin Exp Immunol.; 119(2): 361-367; Feb. 2000.

Ian K Campbell, Alison Bendele, David A Smith, John A Hamilton Granulocyte-macrophage colony stimulating factor exacerbates collagen induced arthritis in mice *Ann Rheum Dis*; 56:364-368 Jun. 1997.

Andrew D Cook, Emma L Braine, Ian K Campbell, Melissa J Rich and John A Hamilton "Blockade of collagen-induced arthritis post-onset by antibody to granulocyte-macrophage colony-stimulating factor (GM-CSF): requirement for GM-CSF in the effector phase of disease" *Arthritis Res*, 3:293-298, 2001.

Yuan H. Yang, John A. Hamilton "Dependence of interleukin-1-induced arthritis on granulocyte-macrophage colony-stimulating factor" vol. 44 Issue 1, pp. 111-119, Jan. 25, 2001.

M K Gorny, V Gianakakos, S Sharpe, and S Zolla-Pazner "Generation of human monoclonal antibodies to human immunodeficiency virus" PNAS vol. 86 No. 5 1624-1628, Mar. 1, 1989.

Tracey L. Bonfield, Mani S. Kavuru and Mary Jane Thomassen "Anti-GM-CSF Titer Predicts Response to GM-CSF Therapy in Pulmonary Alveolar Proteinosis" vol. 105, Issue 3, pp. 342-350, Dec. 2002.

Song XY et al., Coming of age: Anti-cytokine therapies, *Mol Interv.* Feb. 2002;2(1):36-46.

Weiner LM, Fully human therapeutic monoclonal antibodies, *J Immunother.* Jan.-Feb. 2006;29(1):1-9.

Enzler et al., Chapter 21. Granulocyte-macrophage colony-stimulating factor, In: Thomson et al., eds., The Cytokine Handbook, 4th Edition, Elsevier Science Ltd. 2003:503-524.

GENBANK Submission; NIH/NCBI, Accession No. NP_000749; Johnson et al.; Dec. 13, 2010.

GENBANK Submission; NIH/NCBI, Accession No. NP_034099; Choi et al.; Dec. 5, 2010.

GENBANK Submission; NIH/NCBI, Accession No. NP_001028121; Hutchinson et al.; Sep. 9, 2010.

GENBANK Submission; NIH/NCBI, Accession No. AAA52578.1; Lee et al.; Nov. 8, 1994.

GENBANK Submission; NIH/NCBI, Accession No. CAA26820.1; Gough et al.; Sep. 24, 2008.

GENBANK Submission; UniProtein, Accession No. B0KWQ4; Antonellis et al.; Nov. 30, 2010.

BLAST (Basic Local Alignment Search Tool) results for comparison of sequences AAA52578.1 and CAA26820.1. Search performed on Mar. 9, 2010. 3 pages.

Brown et al., Mapping of human granulocyte-macrophage-colony-stimulating-factor domains interacting with the human granulocyte-macrophage-colony-stimulating-factor-receptor alpha-subunit. Eur J Biochem. Nov. 1, 1994;225(3):873-80.

Dempsey et al., Monoclonal antibodies that recognize human granulocyte-macrophage colony-stimulating factor and neutralize its bioactivity in vitro. Hybridoma. Dec. 1990;9(6):545-58. Abstract only.

Jakobovits et al., From XenoMouse technology to panitumumab, the first fully human antibody product from transgenic mice. Nat Biotechnol. Oct. 2007;25(10):1134-43.

Nice et al., Human granulocyte-macrophage colony-stimulating factor (hGM-CSF): identification of a binding site for a neutralizing antibody. Growth Factors. 1990;3(2):159-69. Abstract only.

Scott et al., A phase i dose-escalation study of bibh 1 in patients with advanced or metastatic fibroblast activation protein positive cancer. 2001 ASCO Annual Meeting. Proc Am Soc Clin Oncol. 2001;20:Abstract 1028.

Shanafelt et al., The amino-terminal helix of GM-CSF and IL-5 governs high affinity binding to their receptors. EMBO J. Dec. 1991;10(13):4105-12.

Short et al., Contribution of antibody heavy chain CDR1 to digoxin binding analyzed by random mutagenesis of phage-displayed Fab 26-10. J Biol Chem. Dec. 1, 1995;270(48):28541-50.

Veracity, TGN1412 drug trial update: One patient may lose fingers and toes due to drug side effects. Natural News.com. May 8, 2006. Retrieved Mar. 3, 2010 from http://www.naturalnews.com/019371.html.

Wilkinson, Pharmacokinetics: The dynamics of drug absorption, distribution, and elimination. Chapter 1 in Goodman & Gilman's The Pharmacological Basis of Therapeutics. 10th Edition. McGraw-Hill, New York, NY, 2001:3-29.

\* cited by examiner

SEQUENCE LISTING

<160> NUMBER OF SEQ ID NOS: 14

<210> SEQ ID NO 1
<211> LENGTH: 215
<212> TYPE: PRT
<213> ORGANISM: Homo sapiens

<400> SEQUENCE: 1

Asp Ile Val Leu Thr Gln Ser Pro Gly Thr Leu Ser Leu Ser Pro Gly
1               5                   10                  15

Glu Arg Val Thr Val Ser Cys Arg Ala Ser His Arg Val Ser Ser Asn
            20                  25                  30

Tyr Leu Ala Trp Tyr Gln Gln Arg Pro Gly Gln Ser Pro Arg Leu Leu
        35                  40                  45

Ile Phe Gly Ala Ser Asn Arg Ala Thr Gly Val Pro Asp Arg Phe Ser
    50                  55                  60

Gly Ser Gly Ser Gly Thr Asp Phe Ala Leu Thr Ile Ser Arg Leu Glu
65                  70                  75                  80

Pro Asp Asp Phe Ala Val Tyr Tyr Cys Gln Gln Tyr Ala Ser Ser Pro
                85                  90                  95

Val Thr Phe Gly Gly Gly Thr Lys Leu Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215

<210> SEQ ID NO 2
<211> LENGTH: 452
<212> TYPE: PRT
<213> ORGANISM: Homo sapiens

<400> SEQUENCE: 2

Leu Val Gln Leu Val Gln Ser Glu Ala Glu Val Lys Lys Pro Gly Ala
1               5                   10                  15

Ser Val Arg Ile Ser Cys Arg Thr Ser Gly Tyr Ile Phe Pro Thr Phe
            20                  25                  30

Ala Leu His Trp Val Arg Gln Ala Pro Gly Gln Ser Leu Glu Trp Val
        35                  40                  45

Gly Ser Ile Asn Thr Ala Ser Gly Lys Thr Lys Phe Ser Thr Lys Phe
    50                  55                  60

Gln Asp Arg Leu Thr Leu Ser Ser Asn Thr Ser Ala Thr Thr Val Tyr
65                  70                  75                  80

Met Asp Leu Ser Gly Leu Thr Leu Asp Asp Thr Ala Leu Tyr Tyr Cys

```
                    85                  90                  95
Ala Arg Asp Arg Phe Gln Asn Ile Met Ala Thr Ile Leu Asp Val Trp
                100                 105                 110
Gly Gln Gly Thr Leu Val Thr Val Ser Ser Ala Ser Thr Lys Gly Pro
            115                 120                 125
Ser Val Phe Pro Leu Ala Pro Ser Ser Lys Ser Thr Ser Gly Gly Thr
        130                 135                 140
Ala Ala Leu Gly Cys Leu Val Lys Asp Tyr Phe Pro Glu Pro Val Thr
145                 150                 155                 160
Val Ser Trp Asn Ser Gly Ala Leu Thr Ser Gly Val His Thr Phe Pro
                165                 170                 175
Ala Val Leu Gln Ser Ser Gly Leu Tyr Ser Leu Ser Ser Val Val Thr
            180                 185                 190
Val Pro Ser Ser Ser Leu Gly Thr Gln Thr Tyr Ile Cys Asn Val Asn
        195                 200                 205
His Lys Pro Ser Asn Thr Lys Val Asp Lys Lys Val Glu Pro Lys Ser
    210                 215                 220
Cys Asp Lys Thr His Thr Cys Pro Pro Cys Pro Ala Pro Glu Leu Leu
225                 230                 235                 240
Gly Gly Pro Ser Val Phe Leu Phe Pro Pro Lys Pro Lys Asp Thr Leu
                245                 250                 255
Met Ile Ser Arg Thr Pro Glu Val Thr Cys Val Val Val Asp Val Ser
            260                 265                 270
His Glu Asp Pro Glu Val Lys Phe Asn Trp Tyr Val Asp Gly Val Glu
        275                 280                 285
Val His Asn Ala Lys Thr Lys Pro Arg Glu Glu Gln Tyr Asn Ser Thr
290                 295                 300
Tyr Arg Val Val Ser Val Leu Thr Val Leu His Gln Asp Trp Leu Asn
305                 310                 315                 320
Gly Lys Glu Tyr Lys Cys Lys Val Ser Asn Lys Ala Leu Pro Ala Pro
                325                 330                 335
Ile Glu Lys Thr Ile Ser Lys Ala Lys Gly Gln Pro Arg Glu Pro Gln
            340                 345                 350
Val Tyr Thr Leu Pro Pro Ser Arg Asp Glu Leu Thr Lys Asn Gln Val
        355                 360                 365
Ser Leu Thr Cys Leu Val Lys Gly Phe Tyr Pro Ser Asp Ile Ala Val
    370                 375                 380
Glu Trp Glu Ser Asn Gly Gln Pro Glu Asn Asn Tyr Lys Thr Thr Pro
385                 390                 395                 400
Pro Val Leu Asp Ser Asp Gly Ser Phe Phe Leu Tyr Ser Lys Leu Thr
                405                 410                 415
Val Asp Lys Ser Arg Trp Gln Gln Gly Asn Val Phe Ser Cys Ser Val
            420                 425                 430
Met His Glu Ala Leu His Asn His Tyr Thr Gln Lys Ser Leu Ser Leu
        435                 440                 445
Ser Pro Gly Lys
    450

<210> SEQ ID NO 3
<211> LENGTH: 109
<212> TYPE: PRT
<213> ORGANISM: Homo sapiens

<400> SEQUENCE: 3

Asp Ile Val Leu Thr Gln Ser Pro Gly Thr Leu Ser Leu Ser Pro Gly
```

```
                1               5                  10                 15
Glu Arg Val Thr Val Ser Cys Arg Ala Ser His Arg Val Ser Ser Asn
                    20                 25                 30

Tyr Leu Ala Trp Tyr Gln Gln Arg Pro Gly Gln Ser Pro Arg Leu Leu
            35                 40                 45

Ile Phe Gly Ala Ser Asn Arg Ala Thr Gly Val Pro Asp Arg Phe Ser
    50                 55                 60

Gly Ser Gly Ser Gly Thr Asp Phe Ala Leu Thr Ile Ser Arg Leu Glu
65                 70                 75                 80

Pro Asp Asp Phe Ala Val Tyr Tyr Cys Gln Gln Tyr Ala Ser Ser Pro
                85                 90                 95

Val Thr Phe Gly Gly Gly Thr Lys Leu Glu Ile Lys Arg
                100                105
```

<210> SEQ ID NO 4
<211> LENGTH: 122
<212> TYPE: PRT
<213> ORGANISM: Homo sapiens

<400> SEQUENCE: 4

```
Leu Val Gln Leu Val Gln Ser Glu Ala Glu Val Lys Lys Pro Gly Ala
1               5                  10                 15

Ser Val Arg Ile Ser Cys Arg Thr Ser Gly Tyr Ile Phe Pro Thr Phe
                20                 25                 30

Ala Leu His Trp Val Arg Gln Ala Pro Gly Gln Ser Leu Glu Trp Val
            35                 40                 45

Gly Ser Ile Asn Thr Ala Ser Gly Lys Thr Lys Phe Ser Thr Lys Phe
    50                 55                 60

Gln Asp Arg Leu Thr Leu Ser Ser Asn Thr Ser Ala Thr Thr Val Tyr
65                 70                 75                 80

Met Asp Leu Ser Gly Leu Thr Leu Asp Asp Thr Ala Leu Tyr Tyr Cys
                85                 90                 95

Ala Arg Asp Arg Phe Gln Asn Ile Met Ala Thr Ile Leu Asp Val Trp
                100                105                110

Gly Gln Gly Thr Leu Val Thr Val Ser Ser
            115                120
```

<210> SEQ ID NO 5
<211> LENGTH: 12
<212> TYPE: PRT
<213> ORGANISM: Homo sapiens

<400> SEQUENCE: 5

```
Arg Ala Ser His Arg Val Ser Ser Asn Tyr Leu Ala
1               5                  10
```

<210> SEQ ID NO 6
<211> LENGTH: 7
<212> TYPE: PRT
<213> ORGANISM: Homo sapiens

<400> SEQUENCE: 6

```
Gly Ala Ser Asn Arg Ala Thr
1               5
```

<210> SEQ ID NO 7
<211> LENGTH: 9
<212> TYPE: PRT
<213> ORGANISM: Homo sapiens

<400> SEQUENCE: 7

Gln Gln Tyr Ala Ser Ser Pro Val Thr
1               5

<210> SEQ ID NO 8
<211> LENGTH: 10
<212> TYPE: PRT
<213> ORGANISM: Homo sapiens

<400> SEQUENCE: 8

Gly Tyr Ile Phe Pro Thr Phe Ala Leu His
1               5                   10

<210> SEQ ID NO 9
<211> LENGTH: 16
<212> TYPE: PRT
<213> ORGANISM: Homo sapiens

<400> SEQUENCE: 9

Ser Ile Asn Thr Ala Ser Gly Lys Thr Lys Phe Ser Thr Lys Phe Gln
1               5                   10                  15

<210> SEQ ID NO 10
<211> LENGTH: 13
<212> TYPE: PRT
<213> ORGANISM: Homo sapiens

<400> SEQUENCE: 10

Asp Arg Phe Gln Asn Ile Met Ala Thr Ile Leu Asp Val
1               5                   10

<210> SEQ ID NO 11
<211> LENGTH: 23
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (21)..(21)
<223> OTHER INFORMATION: r is a or g

<400> SEQUENCE: 11
acccagacgg aaccatggaa rcc                                           23

<210> SEQ ID NO 12
<211> LENGTH: 23
<212> TYPE: DNA
<213> ORGANISM: Artificial Sequence
<220> FEATURE:
<223> OTHER INFORMATION: Synthetic Oligonucleotide

<400> SEQUENCE: 12
cacttctccc tctaacactc tcc                                           23

<210> SEQ ID NO 13
<211> LENGTH: 23
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (3)..(3)
<223> OTHER INFORMATION: s is c or g
<220> FEATURE:
<221> NAME/KEY: misc_feature
<222> LOCATION: (12)..(12)

```
<223> OTHER INFORMATION: m is a or c
<220> FEATURE:
<221> NAME/KEY: misc_feature
<222> LOCATION: (13)..(13)
<223> OTHER INFORMATION: w is a or t

<400> SEQUENCE: 13
gascacagct cmwcaccatg gac                                          23

<210> SEQ ID NO 14
<211> LENGTH: 23
<212> TYPE: DNA
<213> ORGANISM: Artificial Sequence
<220> FEATURE:
<223> OTHER INFORMATION: Synthetic Oligonucleotide

<400> SEQUENCE: 14
gccgtcgcac tcatttaccc gga                                          23
```

HUMAN MONOCLONAL ANTIBODY BINDING TO HGM-CSF AND ITS ANTIGEN BINDING PORTION

RELATED APPLICATIONS

This application is Continuation-In-Part Application of International Application No. PCT/JP2006/320502, filed on Oct. 13, 2006, which claims priority of Japanese Patent Application No. 2005-311776, filed on Oct. 26, 2005, the entire content and disclosure of the preceding applications are incorporated by reference into this application.

FIELD OF THE INVENTION

This invention relates to a monoclonal antibody and its antigen binding portion binding to human granulocyte-macrophage colony stimulating factor (described as "hGM-CSF").

DESCRIPTION OF THE BACKGROUND ART

Granulocyte-macrophage colony stimulating factor (GM-CSF) promotes to proliferate bone-marrow granulocyte and macrophage progenitor cells. It was identified as a humoral factor stimulating colonization of granulocyte and macrophage in vitro. Therefore, the factor is named as Granulocyte-macrophage colony stimulating factor (GM-CSF)

GM-CSF is now known as a stimulating factor for a wide range of cells; inducing differentiation and proliferation of granulocyte-macrophage lineage blood cells, stimulating a function of antigen presenting cells, expressing and maintaining a part of epithelial functions and expressing functions of alveolar macrophage (e.g. stimulating surfactant decomposition, stimulating disinfection capacity, and stimulating Fc receptor expression) (The cytokine handbook, 4th edition (ed.) Thomson, A. et al., Academic Press, 2003).

On the other hand, GM-CSF is known to cause various diseases. GM-CSF induces various diseases, such as 1) allergic disease such as asthma, atopy, and pollinosis, 2) graft rejection, graft-versus-host disease (GVHD), and 3) autoimmune diseases such as rheumatoid arthritis.

For example, an overexpressing hGM-CSF is detected in a lung of allergic subject or a joint of chronic rheumatoid arthritis subject. hGM-CSF mRNA is excessively detected in skin of individual with allergy. Furthermore, it is reported that the survival of monocyte, which is an inflammation outbreak cell of atopic dermatitis, is enhanced by GM-CSF production. (Bratton, D. L. et al., Granulocyte macrophage colony-stimulating factor contributes to enhanced monocyte survival in chronic atopic dermatitis. J. Clin. Invest., 95: 211-218, 1995).

Also, it is shown that GM-CSF stimulates proliferation of leukemic cells. Therefore GM-CSF is considered as a factor causing leukemia.

From the above reports, it is considered to be useful for antibody to bind to the over-expressed hGM-CSF in order to depress a biological activity, when a therapy is provided to treat various diseases caused by hGM-CSF.

The hGM-CSF activity is depressed to palliate disease symptom. The anti-hGM-CSF antibody has a high affinity and a high neutralizing capacity against hGM-CSF, and does not show immunological reaction. Therefore, it is estimated to be useful when the anti-hGM-CSF antibody is administered as an antibody agent for human.

So far, it has been reported that anti GM-CSF antibody is effective in a mouse asthma model (Cates, E. C. et al., Intra-nasal exposure of mice to house dust mite elicits allergic airway inflammation via a GM-CSF-mediated mechanism. J. Immunol., 173: 6384-6392, 2004. Ohta, K. et al., Diesel exhaust particulate induces airway hyperresponsiveness in a murine model: essential role of GM-CSF. J. Allergy Clin. Immunol., 104: 1024-1030, 1999.). Also, it is reported that a model mouse for inflammatory arthritis will worsen its symptom, when GM-CSF is administrated. (Bischof, R. J. et al., Exacerbation of acute inflammatory arthritis by the colony-stimulating factors CSF-1 and granulocyte macrophage (GM)-CSF: evidence of macrophage infiltration and local proliferation. Clin. Exp. Immunol., 119: 361-367, 2000. Campbell, I. K. et al., Granulocyte-macrophage colony stimulating factor exacerbates collagen induced arthritis in mice. Annal. Res. Dis., 56: 364-368, 1997.). And, it is also reported that anti GM-CSF antibody is effective for palliating symptom (Cook, A. D. et al., Blockade of collagne-induced arthritis post-onset by antibody to granulocyte-macrophage colony-stimulating factor (GM-CSF): requirement for GM-CSF in the effector phase of disease. Arthritis Res., 3: 293-298, 2001. Yang, Y. H. and Hamilton, J. A., Dependence of interleukin-1-induced arthritis on granulocyte-macrophage colony-stimulating factor. Arthritis Rheumatol., 44: 111-119, 2001.).

Antibodies blocking hGM-CSF reported does not have sufficient affinity and depressing capacity against hGM-CSF, although hGM-CSF is found to induce various diseases.

Therefore, the existing anti hGM-CSF antibodies were not able to inhibit a natural hGM-CSF biologic activity sufficiently (Japanese Patent Application No. H05-176792).

Also, polyclonal antibody and monoclonal antibody were derived from experimental animals, such as mice, rabbits and caprines. However, the obtained antibodies have the sequence specific for each kinds of animals. If they are administered to human body, human immune system recognizes the antibody as a foreign, and then, human anti-animal antibody response (that is, antibody produces its own antibody) is caused as a problem.

Therefore, it is strongly desired to develop an anti hGM-CSF antibody and its antigen binding portion derived from human monoclonal antibody without immunological response, so that they may be applied as a therapeutic agent with higher affinity, specificity and depressing capacity.

This invention focuses on providing a human monoclonal antibody and its antigen binding portion which excel in affinity and depressing capacity on hGM-CSF causing various diseases.

SUMMARY OF INVENTION

In an inventive approach, the inventors found that a human monoclonal antibody is sufficient in affinity and depressing capacity against hGM-CSF. Then, the present invention was achieved.

One embodiment of the present invention relates to a human monoclonal antibody capable of binding to hGM-CSF and neutralizing bioactivity of the hGM-CSF, wherein the anti-hGM-CSF monoclonal antibody has a light chain (L chain) comprising an amino acid sequence of sequence number 1, and has a heavy chain (H chain) comprising an amino acid sequence of sequence number 2.

Another embodiment of the present invention relates to a human monoclonal antibody or its binding portion capable of binding to hGM-CSF and neutralizing bioactivity of the hGM-CSF, wherein the anti-hGM-CSF monoclonal antibody or its antigen binding portion has a light chain variable region (LCVR) comprising an amino acid sequence of sequence number 3, and has a heavy chain variable region (HCVR) comprising an amino acid sequence of sequence number 4.

Yet another embodiment of the present invention relates to a human monoclonal antibody or its antigen binding portion capable of binding to hGM-CSF and neutralizing bioactivity of the hGM-CSF, wherein the anti-hGM-CSF monoclonal antibody or its antigen binding portion has complementarity-determining regions (CDRs), all of which comprise any one amino acid sequence selected from the group of sequence numbers 5 to 10.

Yet another embodiment of the present invention relates to the human monoclonal antibody capable of binding to hGM-CSF and neutralizing bioactivity of the hGM-CSF, wherein the anti-hGM-CSF monoclonal antibody or its antigen binding portion has following CDR domains, the domains comprising: (a) a light chain (L chain) CDR 1 domain having an amino acid sequence of sequence number 5, (b) a light chain (L chain) CDR 2 domain having an amino acid sequence of sequence number 6, and (c) a light chain (L chain) CDR 3 domain having an amino acid sequence of sequence number 7.

Yet another embodiment of the present invention relates to the human monoclonal antibody capable of binding to hGM-CSF and neutralizing bioactivity of the hGM-CSF, wherein the anti-hGM-CSF monoclonal antibody or its antigen binding portion has following CDR domains, the domains comprising: (a) a heavy chain (H chain) CDR 1 domain having an amino acid sequence of sequence number 8, (b) a heavy chain (H chain) CDR 2 domain having an amino acid sequence of sequence number 9, and (c) a heavy chain (H chain) CDR 3 domain having an amino acid sequence of sequence number 10.

Yet another embodiment of the present invention relates to the anti-hGM-CSF monoclonal antibody or its antigen binding portion, wherein the anti-hGM-CSF monoclonal antibody or its antigen binding portion has an affinity (M) for hGM-CSF between $2.0 \times 10^{-10}$ M and $2.3 \times 10^{-10}$ M.

Yet another embodiment of the present invention relates to the anti-hGM-CSF monoclonal antibody or its antigen binding portion, wherein approximately 2 µg/mL of the anti-hGM-CSF monoclonal antibody or its antigen binding portion has a neutralizing capacity equivalent to that of 750- to 1500-dilution of blood serum from a patient suffering from idiopathic alveolar proteinosis.

Yet another embodiment of the present invention relates to the anti-hGM-CSF monoclonal antibody or its antigen binding portion, wherein the anti-hGM-CSF monoclonal antibody or its antigen binding portion inhibits to proliferate peripheral blood dendritic cells.

Yet another embodiment of the present invention relates to the anti-hGM-CSF monoclonal antibody or its antigen binding portion, wherein the antibody belongs to $IgG_1$ (κ) class (subclass).

Yet another embodiment of the present invention relates to a medicinal composition for disease caused by the hGM-CSF comprising: the anti-hGM-CSF monoclonal antibody or its antigen binding portion, and a pharmaceutically acceptable carrier.

Yet another embodiment of the present invention relates to Deoxyribonucleic acid (DNA) coding the anti-hGM-CSF monoclonal antibody or its antigen binding portion capable of binding to hGM-CSF and neutralizing bioactivity of the hGM-CSF, wherein the isolated DNA codes any one of amino acid sequences selected from the group of the sequence numbers 1 to 4, or wherein an isolated DNA codes 3 amino acid sequences selected from the group of the sequence numbers 5 to 10.

Yet another embodiment of the present invention relates to the isolated DNA capable of hybridizing with the DNA described above under stringent condition.

Yet another embodiment of the present invention relates to a vector wherein the isolated DNA is incorporated therein.

Yet another embodiment of the present invention relates to a vector wherein the isolated DNA are incorporated therein, wherein the isolated DNA is capable of hybridizing with the DNA described above under stringent condition.

Yet another embodiment of the present invention relates to a host cell wherein the recombinant expression vector incorporating the isolated DNA is introduced therein.

An anti-hGM-CSF antibody or its antigen binding portion specifically binds to hGM-CSF causing various diseases, and obliterate (neutralize) a bioactivity, so that the anti-hGM-CSF antibody may express high affinity and high neutralizing capacity (to hGM-CSF). The anti-hGM-CSF antibody or its antigen binding portion is made from human monoclonal antibody. Therefore, it does not show immunogenicity and rejection. Furthermore, the anti-hGM-CSF antibody or its antigen binding portion inhibits the proliferation of peripheral blood dendritic cells. Therefore, anti-GM-CSF antibody may contribute an attenuation of antigen-presentation capacity.

These properties are thought to be effective as a prophylactic and a therapeutic agent for graft rejection, graft-versus-host disease (GVHD), for the allergic diseases such as asthma, atopy and pollinosis, and for the autoimmune diseases such as rheumatoid arthritis and so on.

BRIEF DESCRIPTION OF THE DRAWINGS

The hGM-CSF monoclonal antibody or its antigen binding portion according to the present invention will be explained as below.

FIG. 6 shows TF-1 cell proliferation inhibitory effect caused by anti-hGM-CSF antibody according to the present invention.

DETAILED DESCRIPTIONS

Figure 1:
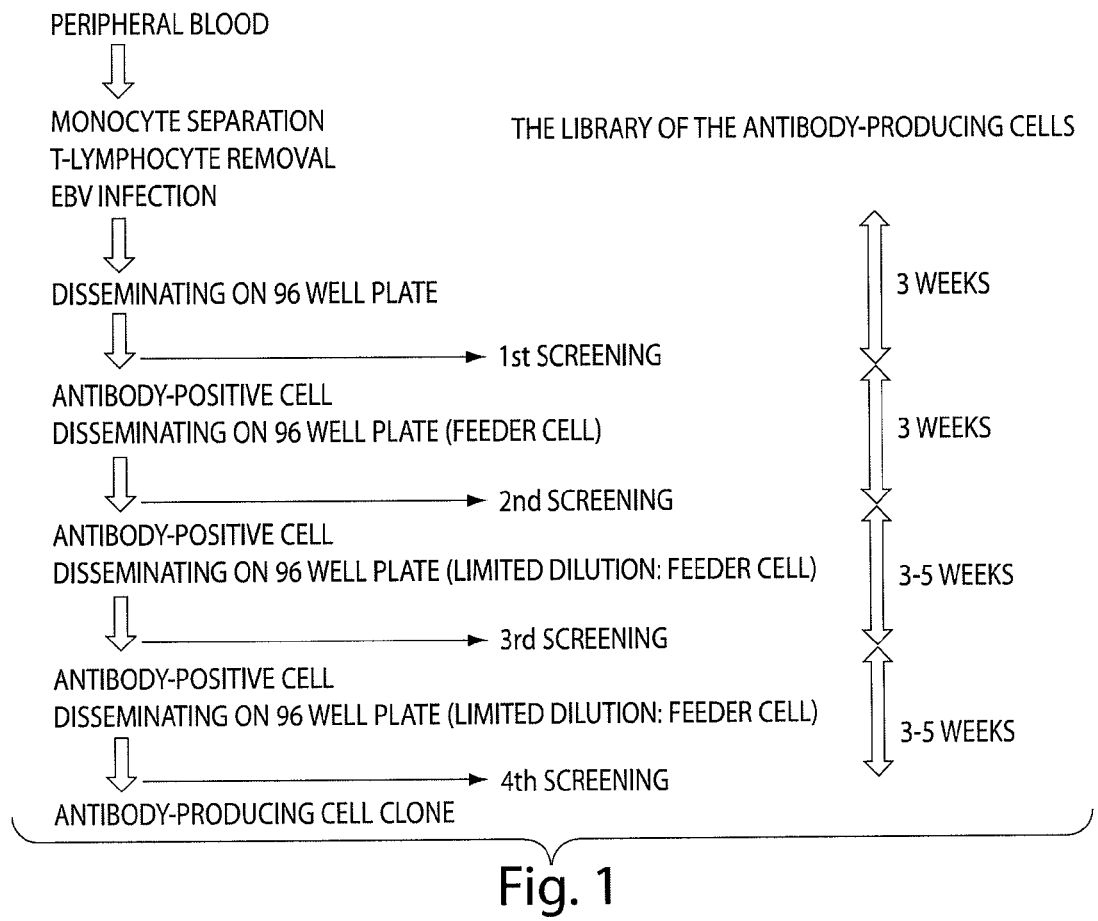
FIG. 1 is a flow chart showing the procedure for separating antibody-producing cell clone of the anti-hGM-CSF antibody according to the present invention.

As used herein, a term "antibody" indicates an immunoglobulin molecule interactively connected with 4 polypeptide chains, 2 heavy chains and 2 light chains with a disulfide bond in the molecule. A term "antigen binding portion" of the antibody (or antigen portion) indicates one or plural antibody fragments with a specific antigen binding activity (e.g. hGM-CSF). A term "neutralizing antibody against the hGM-CSF" indicates the antibody inhibiting bioactivity of the hGM-CSF by binding to the hGM-CSF.

The terms such as "inhibitory effect", "inhibition", "inhibiting" mean a bioactivity depression caused by a natural hGM-CSF antibody. Especially, the terms mean the depression ranged between 5% and 100%. More preferably, for a case of therapeutic purpose, the hGM-CSF bioactivity shows the depression approximately ranged between 50% and 100%.

One aspect of the present invention relates to the human monoclonal antibody capable of binding to hGM-CSF and neutralizing bioactivity of the hGM-CSF, wherein the anti-hGM-CSF monoclonal antibody or its antigen binding portion has a light chain (L chain) comprising an amino acid sequence of sequence number 1, and has a heavy chain (H chain) comprising an amino acid sequence of sequence number 2.

When the human monoclonal antibody or its antigen binding portion binds specifically to the hGM-CSF and depresses the bioactivity, following anti-hGM-CSF monoclonal antibody and its antigen binding portion is also incorporated in the present invention:

anti-hGM-CSF monoclonal antibody and its antigen binding portion, wherein, in the light chain (L chain), the anti-hGM-CSF monoclonal antibody has an amino acid sequence comprising sequence number 1, from which not less than one amino acid is deleted, with which not less than one amino acid is substituted, or to which not less than one amino acid is inserted or added.

anti-hGM-CSF monoclonal antibody, wherein, in the heavy chain (H chain), the anti-hGM-CSF monoclonal antibody has an amino acid sequence comprising sequence number 2, from which not less than one amino acid is deleted, with which not less than one amino acid is substituted, or to which not less than one amino acid is inserted or added.

Each of the heavy chains includes the heavy chain variable region (suitably abbreviated to "HCVR" or "$V_H$") and the heavy chain constant region (the 3 domains, which is abbreviated to "CH1", "CH2", and "CH3"). Each of the light chain includes the light chain variable region (suitably abbreviated to "LCVR" or "$V_L$") and the light chain constant region (a domain abbreviated to "$C_L$"). The HCVR and LCVR are important for the binding specificity of the antibody.

Another aspect of the present invention relates to the human monoclonal antibody or its antigen binding portion capable of binding to hGM-CSF and neutralizing bioactivity of the hGM-CSF, wherein the anti-hGM-CSF monoclonal antibody or its antigen binding portion has a light chain variable region (LCVR) comprising an amino acid sequence of sequence number 3, and has a heavy chain variable region (HCVR) comprising an amino acid sequence of sequence number 4.

When the human monoclonal antibody or its antigen binding portion binds specifically to the hGM-CSF and depresses the bioactivity, following anti-hGM-CSF monoclonal antibody and its antigen binding portion is also incorporated in the present invention:

anti-hGM-CSF monoclonal antibody and its antigen binding portion, wherein, in the light chain variable region (LCVR) and the heavy chain variable region (HCVR), the anti-hGM-CSF monoclonal antibody or its antigen binding portion has the amino acid sequence, from which not less than one amino acid is deleted, with which not less than one amino acid is substituted, or to which not less than one amino acid is inserted or added.

anti-hGM-CSF monoclonal antibody and its antigen binding portion, wherein, in either the light chain variable region (LCVR) or the heavy chain variable region (HCVR), the anti-hGM-CSF monoclonal antibody or its antigen binding portion has the amino acid sequence, from which not less than one amino acid is deleted, with which not less than one amino acid is inserted or added.

The amino acid sequence of the variable region almost rules interaction between the antibody and antigen. A variable region sequence is derived from a natural antibody, and then integrated in a framework sequence derived from a different antibody with a different property. When an expression vector is prepared to have the variable region integrated in the framework, it is possible to express recombinant antibody with natural antibody properties. Therefore, when an intact recombinant antibody is prepared to have the same binding properties as a specific antibody, it is unnecessary to obtain a complete sequence of the antibody. The sequence of the heavy chain and the light chain including the variable region achieves that purpose well.

When the human monoclonal antibody or its antigen binding portion binds specifically to the hGM-CSF and neutralizes the bioactivity, following anti-hGM-CSF monoclonal antibody and its antigen binding portion is also incorporated in the present invention:

the anti-hGM-CSF monoclonal antibody or its antigen binding portion having a variable region comprising number 3 or 4 amino acid sequence, anti-hGM-CSF monoclonal antibody and its antigen binding portion, wherein, in the variable region, anti-hGM-CSF monoclonal antibody or its antigen binding portion has the amino acid sequence coded from which not less than one amino acid is deleted, with which not less than one amino acid is substituted, or to which not less than one amino acid is inserted or added.

The antibody mainly interacts with the target antigen through the amino acid residue on the LCVR and HCVR. Therefore, in the variable regions, there are more various amino acid sequences than those outside the variable region. The HCVR and LCVR are further subdivided into the invariable "framework region (FR)" and the hyper-variable "complementarity determining region (CDR)". The HCVR and LCVR consist of the 3 CDRs and 4 FRs, respectively. Their order is FR1, CDR1, FR2, CDR2, FR3, CDR3, and FR4, from the amino-terminal to the carboxy-terminal.

Another aspect of the present invention relates to the human monoclonal antibody or its antigen binding portion capable of binding to hGM-CSF and neutralizing bioactivity of the hGM-CSF, wherein the anti-hGM-CSF monoclonal antibody or its antigen binding portion has a complementarity-determining region (CDR) coded at least one amino acid sequence selected from the group of sequence numbers 5 to 10.

When the human monoclonal antibody or its antigen binding portion binds specifically to the hGM-CSF and neutralizes the bioactivity, following anti-hGM-CSF monoclonal antibody and its antigen binding portion is also incorporated in the present invention:

anti-hGM-CSF monoclonal antibody and its antigen binding portion, wherein, in the light chain of the complementarity determining region (CDR), the anti-hGM-CSF monoclonal antibody or its antigen binding portion has the amino acid sequence from which not less than one amino acid is deleted, with which not less than one amino acid is substituted, or to which not less than one amino acid is inserted or added.

Another aspect of the present invention relates to the human monoclonal antibody or its antigen binding portion capable of binding to hGM-CSF and neutralizing bioactivity of the hGM-CSF, wherein the anti-hGM-CSF monoclonal antibody or its antigen binding portion has a CDR domain selected from the following groups, the groups comprising:
- (a) a light chain (L chain) CDR 1 domain having an amino acid sequence of sequence number 5,
- (b) a light chain (L chain) CDR 2 domain having an amino acid sequence of sequence number 6,
- (c) a light chain (L chain) CDR 3 domain having an amino acid sequence of sequence number 7.

When the human monoclonal antibody or its antigen binding portion binds specifically to the hGM-CSF and neutralizes the bioactivity, following anti-hGM-CSF monoclonal antibody and its antigen binding portion is also incorporated in the present invention:
  anti-hGM-CSF monoclonal antibody and its antigen binding portion, wherein, in the heavy chain of the complementarity-determining region (CDR), the anti-hGM-CSF monoclonal antibody or its antigen binding portion has the amino acid sequence from which not less than one amino acid is deleted, with which not less than one amino acid is substituted, or to which not less than one amino acid is inserted or added.

Another aspect of the present invention relates to the human monoclonal antibody or its antigen binding portion capable of binding to hGM-CSF and neutralizing bioactivity of the hGM-CSF, wherein the anti-hGM-CSF monoclonal antibody or its antigen binding portion has a CDR domain selected from the following groups, the groups comprising:
- (a) a heavy chain (H chain) CDR 1 domain having an amino acid sequence of sequence number 8,
- (b) a heavy chain (H chain) CDR 2 domain having an amino acid sequence of sequence number 9,
- (c) a heavy chain (H chain) CDR 3 domain having an amino acid sequence of sequence number 10.

When the human monoclonal antibody or its antigen binding portion binds specifically to the hGM-CSF and depresses the bioactivity, following anti-hGM-CSF monoclonal antibody and its antigen binding portion is also incorporated in the present invention:
  anti-hGM-CSF monoclonal antibody and its antigen binding portion, wherein, in the heavy chain of the complementarity-determining region (CDR), the anti-hGM-CSF monoclonal antibody or its antigen binding portion has the amino acid sequence from which not less than one amino acid is deleted, with which not less than one amino acid is substituted, or to which not less than one amino acid is inserted or added.

According to the present invention, the anti-hGM-CSF monoclonal antibody or the antigen binding portion which can bind specifically with a particular antigenic determinant (epitope) and neutralize the bioactivity.

The variations of the anti-hGM-CSF monoclonal antibody or its antigen binding portion are explained as the above description, but the described features may be substituted or convert in the technology field without departing from the scope of the invention.

Namely, in the scope of the present invention, the following antibodies or its antigen binding portions are included:
- (I) the full length antibody
- (II) the antigen binding portion in (I)
- (III) the recombinant human monoclonal antibody capable of specifically binding to hGM-CSF and neutralizing bioactivity, wherein the recombinant human monoclonal antibody is obtained by any well-known techniques, applying the variable region and CDR comprising the amino acid sequence number 3-10, and
- (IV) the recombinant human monoclonal antigen binding portion in (III).

For example, the leader sequences of the heavy chain and light chain are cleaved in the protein maturation process. The cleaved leader sequences have no effect on the final antibody properties.

To complement the cleaved sequence, the cloned cDNA is integrated with the synthetic oligonucleotide in ligation or PCR amplification method.

In an alternative process, a whole variable region is synthesized with a pair of short overlapping oligonucleotide, and then the oligonucleotide is amplified in a PCR amplification method, so that an artificial clone of a variable region is entirely obtained.

Another aspect of the present invention relates to an isolated Deoxyribonucleic acid (DNA) coding the anti-hGM-CSF monoclonal antibody or its antigen binding portion capable of binding to hGM-CSF and neutralizing bioactivity of the hGM-CSF, wherein the isolated DNA codes at least one amino acid sequence selected from the group of the sequence numbers 1 to 10.

When an isolated Deoxyribonucleic acid (DNA) codes the anti-hGM-CSF monoclonal antibody or its antigen binding portion capable of binding to hGM-CSF and neutralizing bioactivity of the hGM-CSF, following anti-hGM-CSF monoclonal antibody and its antigen binding portion is also incorporated in the present invention:
  the isolated DNA capable of hybridizing with the DNA described above under stringent condition.

Following a vector and a host cell is also incorporated in the present invention:
1) A vector incorporating the isolated DNA
2) A host cell integrated with the expression vector Furthermore, applying genetic engineering technique, a phage display method is developed. The phage display method is applied to express a recombinant antibody on the phage surface. Also, the phage display method is applied to artificially shuffle VH and VL genes for preparing a diversified scFv (single chain Fragment of variable region) antibody. It is also possible to obtain a specific antibody by expressing the scFV antibody as phage fusion protein.

This is highly evaluated as a human antigen construction method applied for avoiding immunity and cell fusion technique.

When a specific antibody or its antigen binding portion produced by the above method is applied based on the amino acid sequence number 1-10 described herein, the antibody or its antigen binding portion is also incorporated in the present invention.

The antibody and its antigen binding portion in the present invention may specifically bind to hGM-CSF causing various diseases, and may neutralize the hGM-CSF bioactivity. Especially, the anti-hGM-CSF antibody or its antigen binding portion in the present invention is characterized in its high affinity and high neutralizing activity to the hGM-CSF causing various diseases.

A term "Specific binding" means that the antibody binds to a certain antigen.

Generally, antibody binds to antigen with an affinity of at least about $1×10^{-7}$ M, and binds to a certain antigen with high affinity at least twice in comparison with nonspecific antigens (e.g. BSA, casein).

A term "High affinity" to a certain IgG antibody means an antibody has a binding affinity at least about $1×10^{-7}$ M, preferably at least about $1×10^{-8}$ M, more preferably at least $1×10^{-9}$ M, and much more preferably at least $1×10^{-10}$ M.

Definition of "high affinity" is different among antibody isotypes.

For example, the IgM isotype is defined to have a "high affinity", when it has a binding affinity at least $1×10^{-7}$ M.

The human peripheral blood mononuclear cell and the tumor cell line TF-1 may proliferate, when the hGM-CSF exists. The neutralizing activity of the anti-hGM-CSF antibody or its antigen binding portion is confirmed by measuring the inhibitory effect on their proliferation.

It is known that the human peripheral blood monocyte and the TF-1 cell may proliferate, when cultivated in hGM-CSF. Coexisting with the anti-hGM-CSF antibody or its antigen binding portion in the culture system may inhibit their proliferation.

Generally, the anti-hGM-CSF antibody or its antigen binding portion in the present invention has affinity: Kd= $2.0×10^{-10}$ M–$2.3×10^{-10}$ M.

Approximately 2 μg/mL of the anti-hGM-CSF monoclonal antibody or its antigen binding portion has a neutralizing capacity equivalent to that of a 750- to 1500-dilution of blood serum from a patient suffering from idiopathic alveolar proteinosis.

The anti-hGM-CSF antibody or its antigen binding portion in the present invention specifically may bind to hGM-CSF, and neutralize the hGM-CSF bioactivity. Furthermore, the proliferation of peripheral blood dendritic cells may be inhibited.

Therefore, the anti-hGM-CSF antibody or its antigen binding portion may effectively work for the graft rejection and graft-versus-host disease caused by hyperactivity of antigen-presenting cell.

Another aspect of present invention relates to the anti-hGM-CSF antibody, wherein the anti-hGM-CSF antibody belongs to IgG1 (K) class (subclass). It is known that the IgG antibody has a high affinity and stability.

On the other hand, IgM antibody is known to aggregate itself rapidly and to have low affinity.

The anti-hGM-CSF antibody or its antigen binding portion in the present invention has high affinity and neutralizing capacity to the hGM-CSF. Therefore, it is expected to be applied as therapeutic agents for the various diseases caused by the hGM-CSF, such as allergic dermatitis, asthma, and autoimmune diseases including rheumatoid arthritis.

Furthermore, it affects to inhibit the peripheral blood dendritic cell proliferation. Therefore, it may effectively work for the graft rejection and graft-versus-host disease caused by hyperactivity of the antigen-presenting cell.

As used herein, the term of "a disease caused by hGM-CSF" includes any diseases that cause and worsen the pathophysiology, when a subject has a GM-CSF. The term also includes other diseases that cause and worsen the pathophysiology. It is expected that inhibiting the biological activity of GM-CSF may palliate the disease symptoms caused by GM-CSF, and/or may palliate the disease progression.

For example, GM-CSF may be detected in the biological fluid by applying the anti-GM-CSF antibody. By increasing a GM-CSF concentration in the subject's biological fluid, it is possible to assess whether the subject suffers from the disease or not (For example, increasing GM-CSF concentration in blood serum, blood plasma, and synovial fluid in the subject).

Furthermore, anti-hGM-CSF monoclonal antibody or its antigen binding portion in the present invention is obtained from an antibody-producing cell derived from the blood of the idiopathic alveolar proteinosis patient. Accordingly, the anti-hGM-CSF monoclonal antibody or its antigen binding portion in the present invention is a complete human monoclonal antibody. Therefore, it does not show immunogenicity or rejection response, when the antibody preparation is administered to human body. In the present invention human monocyte is applied in the process of the antibody production, and the monocyte works for preparing the human antibody in the same status as prepared inside the human body. Therefore the antibody is more active than that prepared by mouse etc. For example, the administered dosage of the antibody in the present invention is expected to be reduced to $\frac{1}{50}$–$\frac{1}{100}$ with respect to the dosage of the antibody prepared by mouse etc. in order to obtain the same extent of the therapeutic effect.

Medicinal compositions suitable for administration to a subject may incorporate the antibody and its antigen binding portion of the present invention therein. Typically, the medicinal compositions include the antibody or its antigen binding portion in the present invention, and carrier acceptable for pharmaceutical agent.

As used herein, "the carrier acceptable for pharmaceutical agent" includes any or all of physiologically compatible solution, dispersion medium, coating agent, antimicrobial agent or antifungal agent, osmolar adjustment agent, and absorption retardant. Examples of the carrier acceptable for pharmaceutical agent includes one or plural kinds of agents and their combinations such as water, salt solution, phospharate-buffered saline, dextrose, glycerol and ethanol. In many cases, osmolar adjustment agent such as sugar, polyalchohol or sodium chloride is preferably included in the compositions. The polyalchohol may include mannitol or sorbitol. Furthermore, the carrier acceptable for pharmaceutical agent may include a small amount of auxiliary substances such as humectant, emulsifier, preservative, and buffer agent. The auxiliary substances may enhance preservation or effectivity in the compositions of antibody or its antigen binding portion.

Medicinal compositions suitable for parenteral administration may incorporate the antibody and its antigen binding portion of the present invention therein. Preferably, the antibody or its antigen binding portion is adjusted for the injectable solution containing the antibody at the amount of 0.1~250 mg/ml.

The injectable solution formed in liquid or lyophilized dosage may be prepared in flint or amber vial, ampule, or prefilled syringe. As a buffering agent L-histidine may be used between pH5.0~7.0 (pH6.0 is the best suited). The L-histidine concentration of 5~10 mM may be the best suited. Other agents suitable for the buffering agent may be sodium succinate, sodium citrate, sodium phosphate, or potassium phosphate, but not limited to them. Sodium chloride may be applied to the buffering agent in order to remove toxicity in the solution at the concentration of 0~300 mM (regarding the dosage formed in the liquid, 150 mM is the best suited). The lyophilized dosage form may include a cryoprotectant; mainly sucrose at the ratio of 0~10% (the ratio of 0.5~1.0% may be the best suitable). Other agents suitable for the cryoprotectant may be trehalose and lactose. The lyophilized dosage form may include expander, mainly include mannitol at the ratio of 1~10% (the ratio of 2~4% may be the best suitable). As a stabilizer, mainly L-methionine at the concentration of 1~50 mML (5~10 mM may be the best suited) may be applied to both of the dosages formed in liquid or lyophilization. Glycine and arginine are included in the other appropriate expanders. Polysorbate 80 may be included as a surfactant at the ratio of 0~0.05% (the ratio of 0.005~0.01% may be the best suited). Other surfactant includes polysorbate 20 and BRIJ surfactant, but not limited to them.

Various dosage forms are applicable to the compositions in the present invention. For example, the compositions may have the dosages formed in liquid, semisolid, and solid. Solution (for example, injectable or transfusable solution), dispersion liquid, suspension liquid, tablet, pill, powder, liposome and suppository are included. Preferably, the dosage forms depend on the administration method and the therapeutic example. Preferably, the compositions have the dosages formed in liquid capable of injection and fluid transfusion. For example, the compositions may include other antibodies applied to human passive immunization. The compositions may be preferable for the parenteral administration (for example, intravenous administration, subcutaneous administration, abdominal administration, and intramuscular administration may be shown). In the preferred embodiment, the antibody is administered through intravenous infusion solution or intravenous injection. In another preferred embodiment, the antibody is administered through intramuscular injection or subcutaneous injection.

The compositions for therapies should be generally produced and stored under sterilized and stable condition. The compositions may be prescribed in solution, microemulsion, dispersion liquid, liposome or other structures suitable for the high drug level. The sterilized solution capable of injection is prepared by the following procedures. Required amount of active compounds (specifically, antibody and its antigen binding portion) are mixed in appropriate solvent. If necessary, the one or the combination of the above-mentioned compounds is mixed in appropriate solvent together with the active compounds, and then sterilized by filtration so that the solution is prepared. Generally, fundamental dispersion medium and the active compounds are mixed in sterilized vehicle including other required compounds from the above-mentioned medium. When sterilized lyophilized powder is used to prepare the sterilized injectable solution, vacuum drying and spray drying method are preferably applied as the preparation methods. Through the preparation method, any other desirable compositions are obtained from the active ingredient powder and the sterilized solution applied for the filtration. The water condition of the solution is appropriately sustained by the following means. The means are, for example, applying coating material such as lecithin, maintaining the particle size required for the dispersion liquid, and applying surfactant agent. Pharmaceutical absorption retardants such as monostearic acid and gelatin are included in the compositions, thereby the injectable compositions may be absorbed in human body for a long duration.

The antibody and its antigen binding portion of the present invention may be administrated through the various methods known in the art. The administration routes/methods such as subcutaneous injection, intravenous injection, or fluid transfusion are preferably applied in the various therapies. The administration routes/methods depend on the expected results. Those skilled in the art may understand that implant, percutaneous patch and drug delivery system are included in the administration routes/methods. In one embodiment, the antibody such as controlled release dosage, which may control the release of the compounds, is also applied together with the active compounds for the preparation. Biocompatible polymer has biodegradability. The preparation may include the biocompatible polymer such as ethylene vinyl acetate, polyanhydride, polyglycolic acid, collagen, poly-ortho esters, and polylactate. Various methods for preparing these dosages are granted as patents, and are generally known to those skilled in the art.

In one embodiment, the antibody and the anti binding portion are orally administrated with, for example, the inactive diluent or edible and absorbable carrier. Compounds (and if desired, other ingredients) may also be encapsulated in hard or soft gelatin capsule, compressed in tablet, or directly mixed in food for the subject. In oral administration applied in the therapy, the compounds may be mixed in the excipient, and be used in the forms capable of the ingestion, such as tablet, buccal tablet, troche, capsule, elixir, suspension liquid, syrup, and oblate. It is necessary to coat the compounds in materials preventing from their inactivation, and to administrate the compounds and the materials at the same time.

It is also possible to supplementarily incorporate active compounds in the compositions. In one embodiment, the antibody or its antigen binding portion in the present invention is prescribed with one or plural other therapeutic agents useful for remedying the diseases caused by GM-CSF, or is administrated with other therapeutic agents at the same time. For example, the anti-hGM-CSF antibody or its antigen binding portion of the present invention is prescribed with one or plural other antibodies (for example, antibodies binding to other cytokines or antibodies binding to cell-surface molecules) binding to other targets, or is administrated with other antibodies. Furthermore, it is possible to apply one or plural antibodies of the present invention in combination with two or more kinds of the therapeutic agents. The combination therapy has an advantage that the therapeutic agents work effectively in the small amount. The therapeutic agents enable to avoid the toxicity or complication, both of which might be accompanied with various monotherapies.

Medicinal compositions including carriers pharmaceutically acceptable in the anti-hGM-CSF antibody or its antigen binding portion are considered to be effective against the diseases caused by hGM-CSF. The diseases caused by the excessive production of the hGM-CSF may be illustrated such as (a) allergic disease such as asthma, atopy, and pollinosis, (b) graft rejection, graft-versus-host disease (GVHD) and (c) autoimmune disease such as rheumatoid arthritis.

Now, a process for obtaining the anti-hGM-CSF monoclonal antibody and its antigen binding portion is explained, but not limited to the description of the present invention. The described features may be substituted in the technology field without departing from the scope of the invention.

Anti-hGM-CSF monoclonal antibody and its antigen binding portion of the present invention are derived from the blood obtained from idiopathic alveolar proteinosis patient through the following steps: isolating a cell clone to produce the antibody, selecting an antibody-positive cell from the obtained library of antibody-producing cells, and purifying the antibody obtained from the supernatant of the antibody-positive cell by affinity purification.

1) Separation of Anti-hGM-CSF Antibody-producing Cell Clone

The monocyte of the anti-hGM-CSF antibody is isolated from the blood of a patient, who is suffering from idiopathic alveolar proteinosis (IPAP) and has high level of anti-hGM-CSF antibody in the blood serum. After the removal of T-cell from the monocyte, the monocyte is immortalized. Some immortalizing methods are known. As the example, an inducible factor of cancer, "Epstein-Barr virus" (described as EBV hereinafter) is applied in the transform method (D. Kozbor et al.) for the immortalization. More specifically, the monocyte is infected with EBV, and is immortalized. The immortalized monocyte is proliferated and is kept for a library of the antibody-producing cells.

2) Isolation of the Monoclonal Antibody from the Library of the Antibody-producing Cells Using the known method commonly applied in producing a monoclonal antibody, a monoclonal cell is selected from library of the immortalized cells. More specifically, the desired monoclonal antibody is extracted by the following procedures: cloning the immortalized monocyte by limiting dilution method etc, selecting the monocyte which produces the desired antibody (antibody showing positive reaction to hGM-CSF), cultivating it in culture media for its proliferation, so that the desired monoclonal antibody is extracted from the supernatant of culture media.

From the library of the antibody-producing cells, the lymphocyte producing antibody, which shows positive reaction to hGM-CSF, is selected in order to produce the antibody. More specifically, cell population (clones) showing positive reaction to hGM-CSF is selected by limiting dilution method. It is preferable to employ ELISA using GM-CSF and mouse anti-GM-CSF antibody labeled for detecting a fraction binding to GM-CSF. The cell population (clones) that produces only the desired antibody is obtained by cultivating the selected antibody-positive cell and screening them repeatedly. The steps until the "isolating an antibody-producing cell clone" are illustrated in a flow chart shown in FIG. 1.

3) Affinity Purification Using Protein A

When purifying the anti-hGM-CSF antibody, it is possible to cultivate the selected immortalized cell in a Roller bottle, 2-litter spinner flask, or other cultivating systems. The supernatant is filtrated and concentrated. Then, the protein is purified by affinity chromatography with Protein A-Sepharose (New Jersey, Piscataway, Pharmacia Corp.). After the exchange of the buffering solution to PBS, the concentration of the protein is measured by OD at 280 nm and calculated using absorption coefficient of 1.43, or preferably by nephelometer analysis. The antibody isotype is examined by gel electrophoresis method and antigen specific method.

The obtained anti-hGM-CSF antibody is a complete human antibody produced from B-lymphocyte sensitized in human body, thereby the anti-hGM-CSF antibody may not show the adverse reaction. While the antibody-producing cell is cloned, B-lymphocyte is infected with EB virus, and is infinitely proliferated (immortalization) by the EB virus activity. Accordingly, it is characterized that the antibody-producing cell is cloned by applying such the EB virus activity. The method for immortalization using EB virus has an advantage in producing a natural antibody in a human body. For example, anti-hGM-CSF antibody is 50-100 times as active as an antibody produced by artificially-immunized mouse. A library includes a group of the B-lymphocytes immortalized by the EB virus infection. It is possible to isolate a specific antibody-producing cell clone from the library and obtain a human antibody.

As mentioned above, the described features may be substituted or converted in the technology field without departing from the scope of the invention. When a nucleic acid, a vector and a host cell may express the antibody or its antigen binding portion in the present invention, these are also included in the present invention.

EXAMPLES

Hereinafter, examples of the present invention will be described more specifically, but the examples do not limit the scope of the present invention.

1. Isolation of a hGM-CSF Antibody-producing Cell Clone

The step until the "isolating an antibody-producing cell" is illustrated in a flow chart shown in FIG. 1. A monocyte was separated from human blood having high level of an anti-hGM-CSF antibody in the blood serum. A T-cell was removed from a monocyte. Then monocyte was infected to EBV, so that the cell was proliferated. The proliferated cells were included in the antibody-producing cell library.

The antibody-producing cell library is disseminated in 96 well plate. After about 3-4 weeks cultivation, 1st screening was conducted on the anti-hGM-CSF antibody in the supernatant solution. The ELISA method was applied to screen the anti-hGM-CSF antibody in the 96 well plate on which recombinant GM-CSF was coated. The obtained groups of antibody-positive cells were disseminated on another 96 well plate in low counts, and then a feeder cell was added to the group of cells to accelerate cell proliferation. After 3-4-week cultivation, 2nd screening was conducted on the anti-hGM-CSF antibody. The obtained groups of antibody-positive cells was disseminated on another 96 well plate by limited dilution. In this stage, a feeder cell was also added to the group of cells to accelerate its proliferation. After 3-5 weeks cultivation, 3rd screening was conducted on the anti-hGM-CSF antibody. The obtained group of antibody-positive cell was cultivated by limiting dilution, and was screened, so that an antibody-positive cell clone was obtained on a plate where one cell was disseminated per a well.

2. Identification of Antibody Isotype

Figure 2:
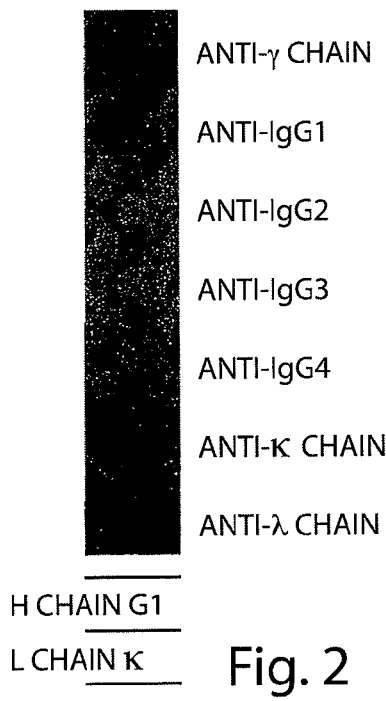
FIG. 2 shows the ELISA result indicating the anti-hGM-CSF antibody isotype according to the present invention.

The isotype of the antibody, which is produced by selected antibody-positive cell clone, was identified by ELISA method as used in the screening. And then a specific antibody was applied to each of isotype as a second antibody. Supernatant of cell culture solution was applied as a sample. Then, it shows that an obtained anti-hGM-CSF antibody belongs to $IgG_1\kappa$ (shown in FIG. 2).

3. Purification of Antibody

Figure 3:
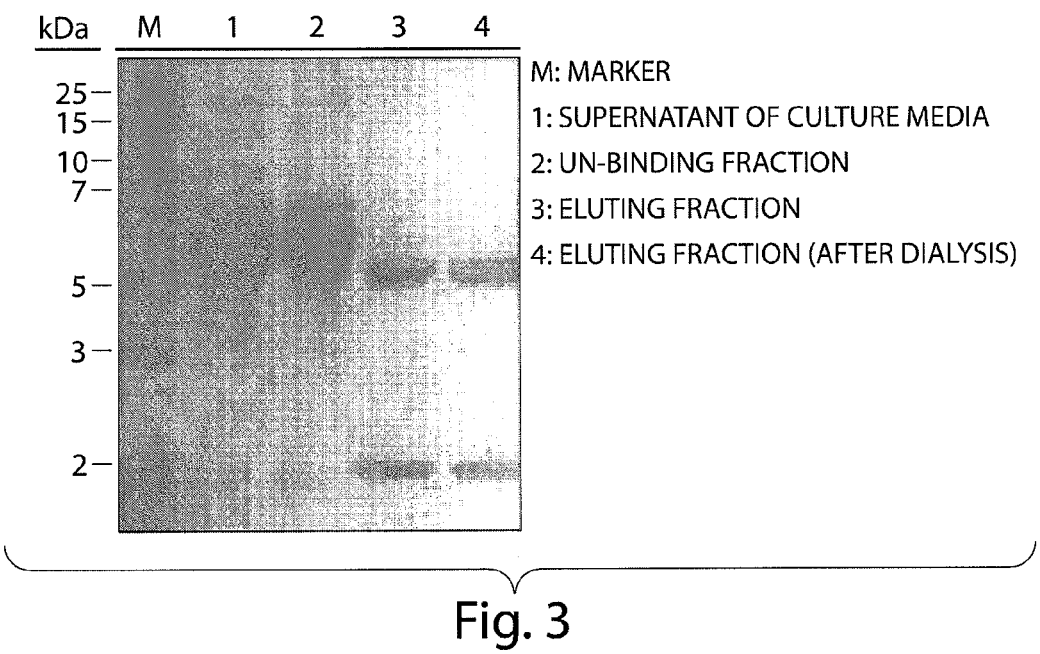
FIG. 3 shows the SDS-PAGE result of anti-hGM-CSF antibody according to the present invention.

Purification of an anti-hGM-CSF antibody was conducted by affinity purification method using Protein A. HiTrap rProtain A FF (Amersham) was applied as a prepacked column, and purification condition was set based on the condition recommended by column manufacturer. FIG. 3 shows a SDS-PAGE result. After the purification, 50 kDa H chain antibody and 25 kDa L chain antibody were observed. Applying the ELISA method, the purified antibody was observed to have anti-GM-CSF antibody activity.

4. Affinity Analysis on Anti-hGM-CSF Antibody

Figure 4:
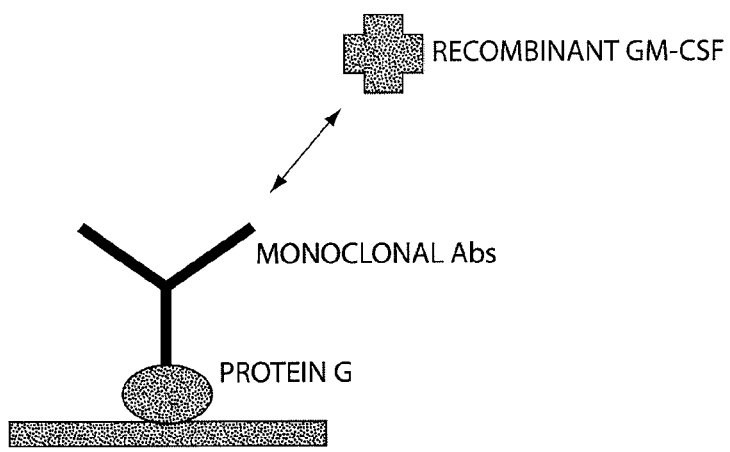
FIG. 4 is a schematic view showing the affinity analysis procedure of anti-hGM-CSF antibody according to the present invention.
Figure 5:
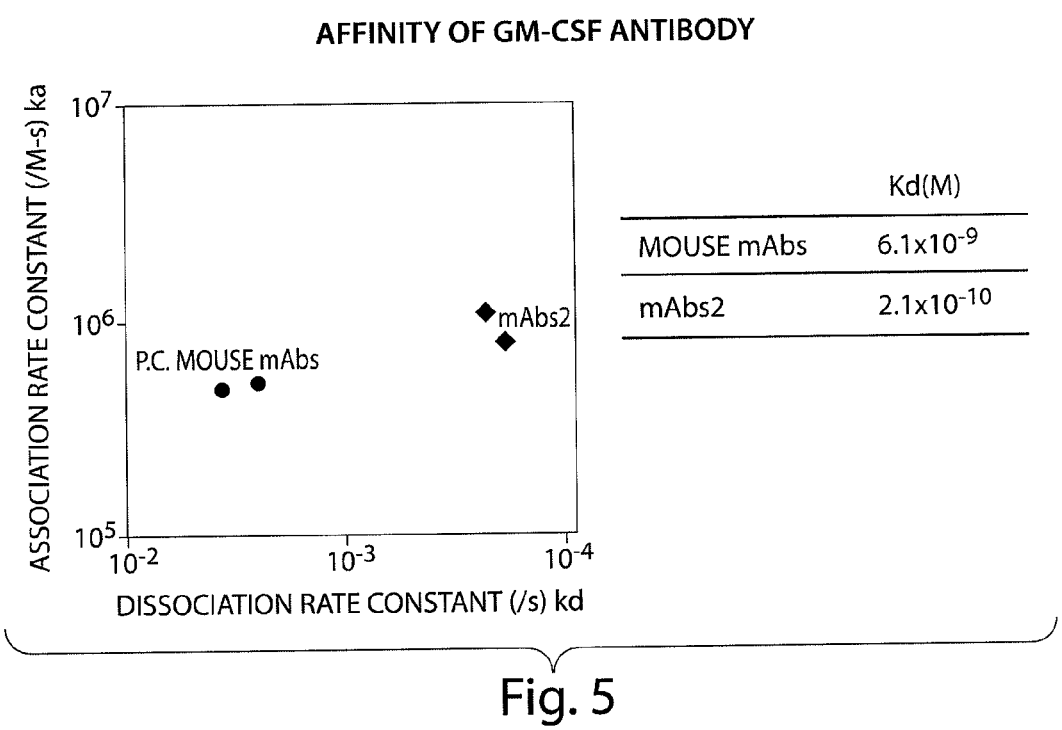
FIG. 5 shows dissociation constant (M) indicating the affinity of anti-hGM-CSF antibody according to present invention.

Affinity analysis was conducted on the anti-hGM-CSF antibody applying BIAcore® system (FIG. 4). In the method, the antibody (purified antibody) was immobilized to a sensor chip, and then an antigen (recombinant) was added to the surface of the immobilized antibody, so that the interaction between antibody and an antigen was measured. A purified antibody was applied to the antibody, and a recombinant hGM-CSF was applied to the antigen. A mouse anti-GM-CSF monoclonal antibody (commercially available) (R&D) was applied to a positive control, and a purified anti-human cytomegalovirus monoclonal antibody was applied to a negative control. After the analysis, it turned out that antigen-antibody interaction was not detected in the negative control. In the positive control, dissociation constant of $6.1\times10^{-9}$ M is shown as the affinity. The affinity of the anti-GM-CSF antibody obtained was $2.1\times10^{-10}$ M (FIG. 5).

5. Evaluation on Neutralizing Activity of the Anti-GM-CSF Antibody

A neutralizing activity was observed for the purpose of evaluating the effectiveness of the anti-GM-CSF antibody. For evaluating the neutralizing activity, TF-1 cell, which proliferate GM-CSF dependently, was applied. A purified antibody and a recombinant GM-CSF were added to the TF-1 cell, and the TF-1 cell was cultivated. After the 3-day cultivation, the number of viable cells was counted. When the antibody indicate the neutralizing activity, it is possible for the antibody to depress the added GM-CSF, and to kill the TF-1 cell. The cell was counted by the Cell Counting Kit (DOJIN), and then evaluated by the color intensity (A450). FIG. 6B shows the evaluation result of the neutralizing activity in anti-GM-CSF antibodies and SFM applied as a control. It shows a variation of the number of the viable cells of TF-1 according to the GM-CSF concentration.

Figure 6A:
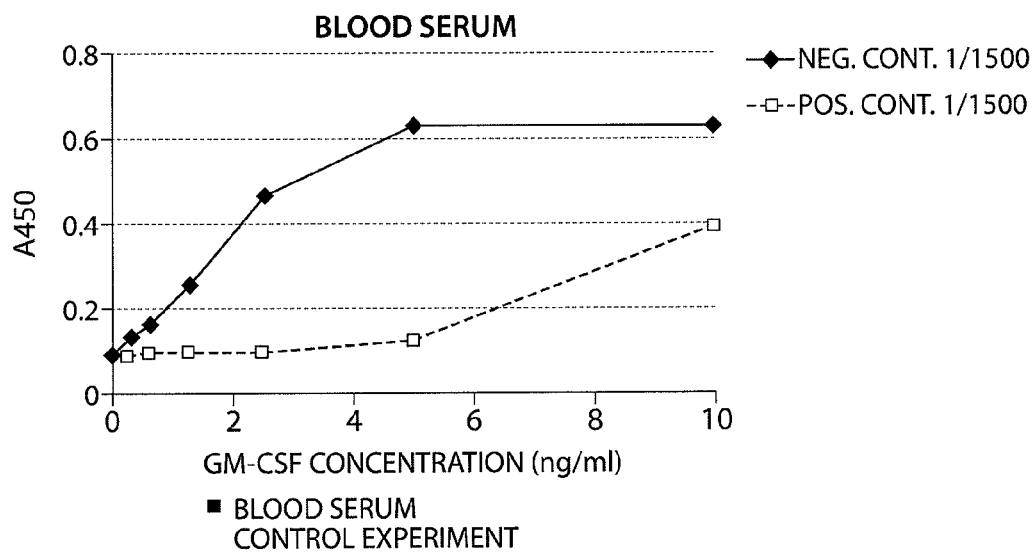
FIG. 6A is a graph showing results from a control experiment. The absorbance at 450 nm ($A_{450}$ versus GM-CSF concentration is shown in the presence of a negative and positive blood serum control.
Figure 6B:
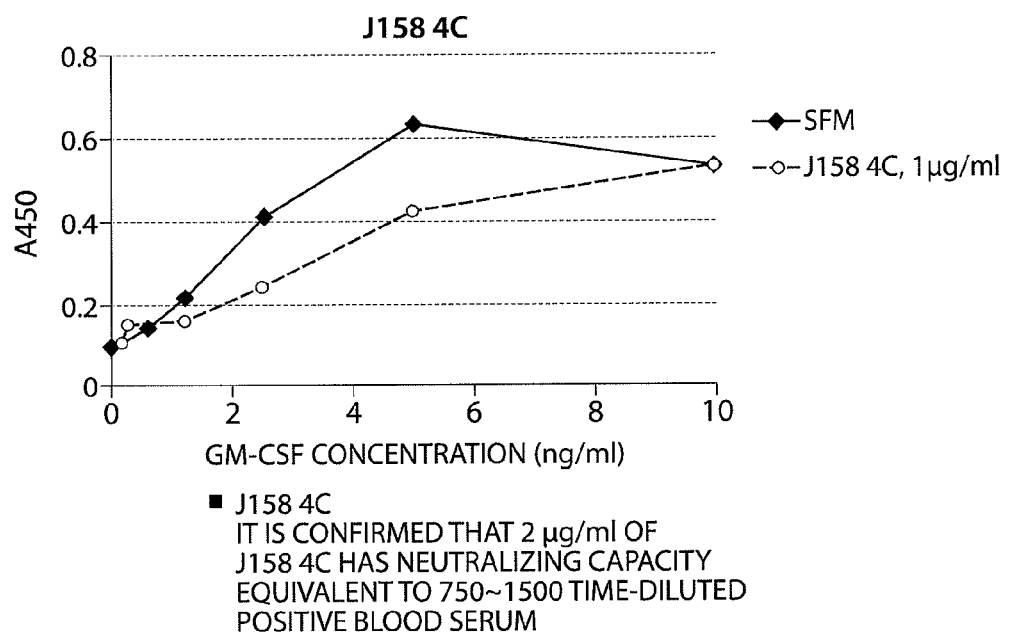
FIG. 6B is a graph showing the $A_{450}$ values versus GM-CSF concentration in the presence of serum free media (SFM) and J158 4C antibody.
Figure 6C:
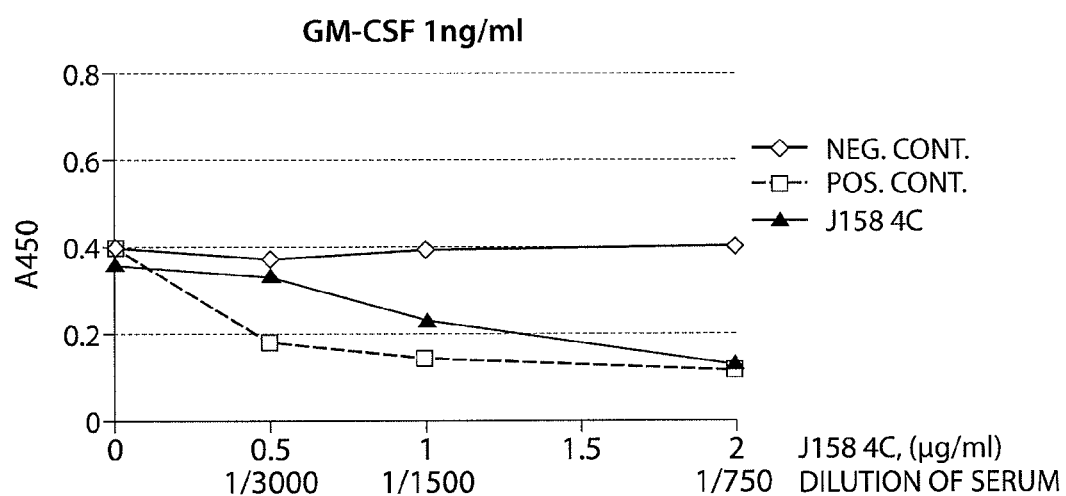
FIG. 6C is a graph showing the $A_{450}$ values versus antibody concentration (J158 4C antibody) or dilution of blood serum (negative and positive blood serum control) in the presence of GM-CSF.

Control experiment was conducted on blood serum (FIG. 6A). Blood serum of a normal subject (negative control) and blood serum of a patient suffering from idiopathic alveolar proteinosis (positive control) were diluted at 1500 times. As a result, it was observed that the TF-1 cell in the blood serum from the normal subject was increased depending on GM-CSF concentration. On the other hand, some of the TF-1 cells in the blood serum of the patient were not increased up to 5 ng/ml of GM-CSF. A further experiment was conducted on the purified antibody J158 4C according to 4 levels of the purified antibody concentration set in 0, 500, 1000, 1500, and 2000 ng/ml. FIG. 6C shows that the number of viable cells was decreased depending on the antibody concentration, and a neutralizing activity was recognized.

Figure 7:
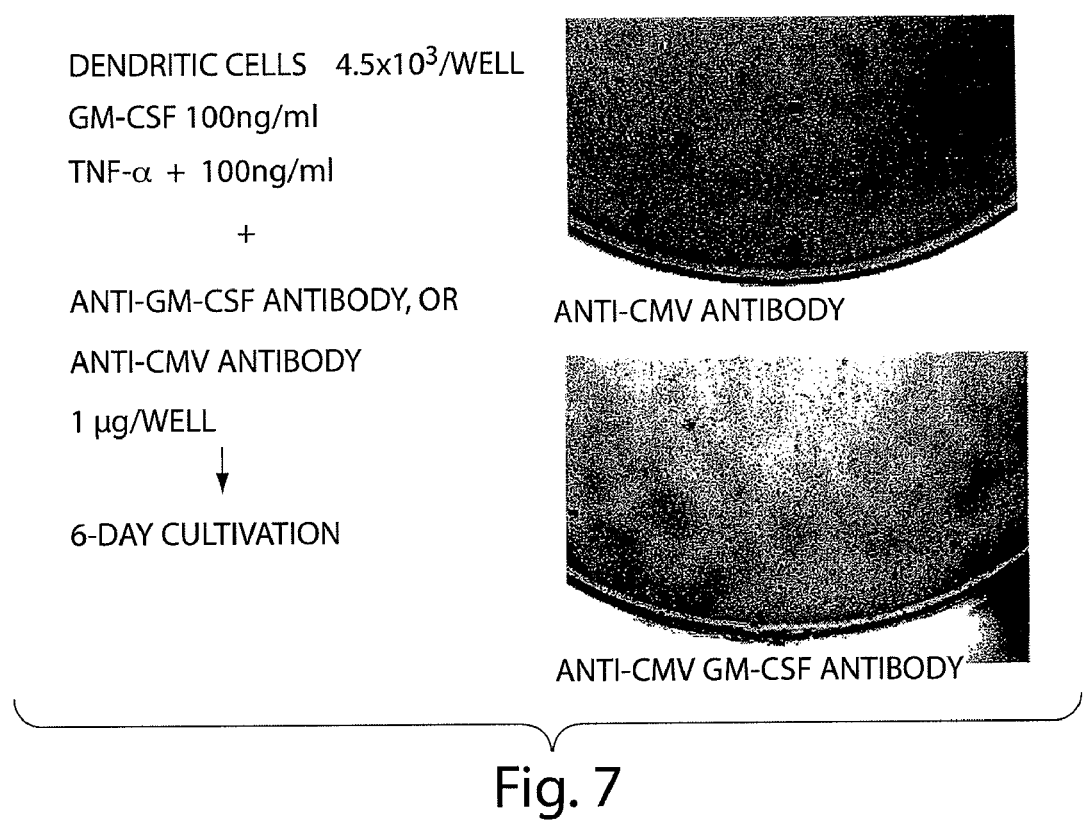
FIG. 7 shows an inhibition ability against proliferation of dendritic cells caused by anti-hGM-CSF antibody according to the present invention.

6. Proliferation Inhibitory Effect Caused by Anti-GM-CSF Antibody on Peripheral Blood Dendritic Cells (FIG. 7)

A monocyte fraction was obtained from the peripheral blood of 20 ml, and DC (a dendritic cell) of $3 \times 10^5$ cells were collected with Blood Dendritic Cell Isolation Kit II Human (Miltenyi Biotec Inc, Auburn Calif., USA). The collected DCs include plasmacytoid DC and myeloid DC. The obtained DCs were cultured in media in which recombinant GM-CSF (100 ng/ml) and TNF-α (100 ng/ml) are added to RPMI1640+10% FCS. The culture solution was disseminated on 96 well Flat Plate at $0.45 \times 10^4$ cells/well, and the cytokine and antibody in the culture solution were newly exchanged on 2nd, 4th, and 6th day. The obtained DC was cultivated for 8 days. As a result, the addition of anti-GM-CSF antibody (1 µg/ml) inhibited a GM-CSF dependent proliferation of the DC. On the other hand, the anti-CMV antibody applied as a control did not inhibit the GM-CSF dependent proliferation of the DC. As mentioned above, it turns out that the anti-GM-CSF antibody inhibits the DC proliferation, and it is estimated that the anti-GM-CSF antibody may attenuate antigen-presenting capacity.

7. Gene Cloning of the Antibody from Antibody-producing Cell

Antibody gene was cloned by PCR method. Total-RNA was extracted from an anti-GM-CSF antibody-producing cell clone with TRIZOL reagent (invitrogen). A cDNA was synthesized with Oligo-dT Primer (invitrogen) and Reverse Transcriptase (invitrogen) obtained from the extracted total-RNA. In the case of both H-chain and L-chain, their antibody genes code the variable regions on their 5'-terminal sides, and their sequences are variable according to the antibody. 3'-terminal sides of their antibody genes code constant regions, and constant domains are conserved among antibody genes. Based on a database of antibody gene sequences, primers described below were designed to contain a transcription initiation point on the 5'-terminal side, and a transcription termination portion on the 3'-terminal side. And then, antibody gene amplification was conducted by using synthesized cDNA as a template.

TABLE 1

|  | SEQ ID NO: |
|---|---|
| light chain: |  |
| Light-kappa FW primer (5'-ACCCAGACGGAACCATGGAARCC-3') | 11 |
| Light-kappa RV primer (5'-CACTTCTCCCTCTAACACTCTCC-3') | 12 |
| heavy chain: | 13 |
| Heavy-gamma FW primer (5'-GASCACAGCTCMWCACCATGGAC-3') |  |
| Heavy-gamma RV primer (5'-GCCGTCGCACTCATTTACCCGGA-3') | 14 |

8. Determination of Amino Acid Sequence in an Antibody Based on a Base Sequence of an Antibody Gene Antibody gene base sequence was determined with ABI sequencer. In anti-GM-CSF antibody based on the obtained base sequence, an amino acid sequence is indicated by sequence numbers 1 through 10.

Figure 8:
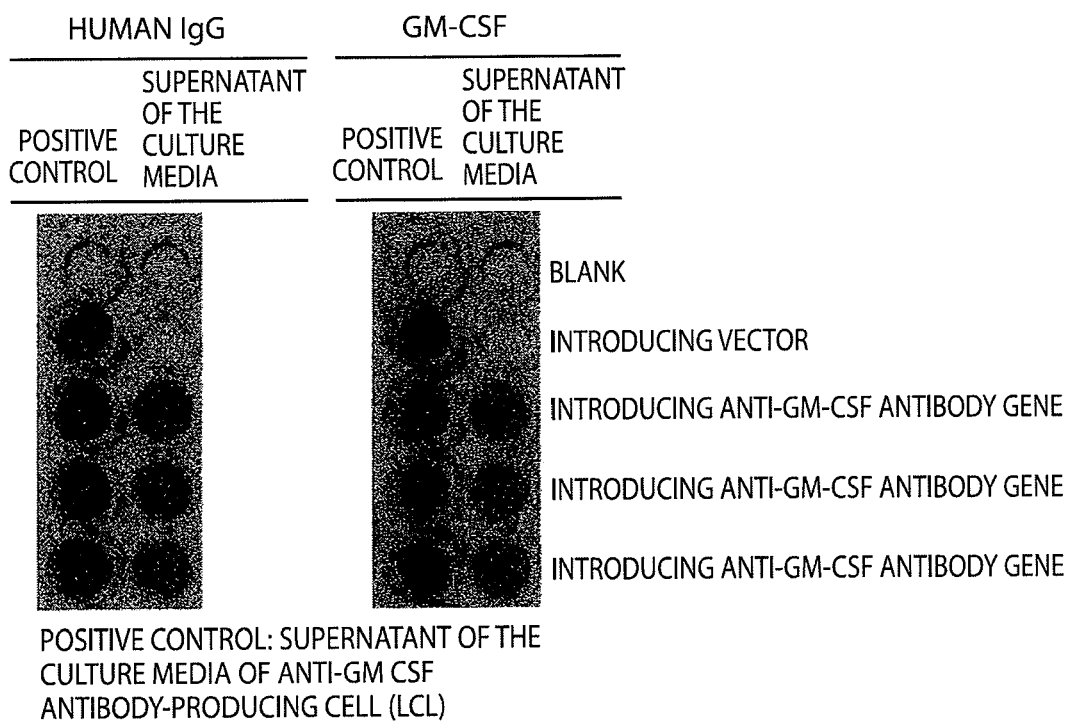
FIG. 8 shows an anti-hGM-CSF antibody production caused by introducing anti hGM-CSF antibody gene to 293T cell.

9. Confirmation on Obtained Antibody Gene Coding an Anti-GM-CSF Antibody (FIG. 8)

cDNA clones of the obtained antibody gene (H-chain, L-chain) were inserted into plasmid vector pSG5 respectively. Both plasmids were introduced to 293T cell, and it is confirmed that antibody was transiently expressed. For transfection of plasmids, Lipofectamine (invitrogen) and Plus reagent (invitrogen) were used. pEGFP was transfected as a control, and transfection efficiency was confirmed by observing GFP expression cell under a fluorescence microscope. The efficiency was 50% to 60%. On the second day after the transfection, 293T cell lysate was applied to conduct the Western blot for detecting human antibody. For detection, peroxidase label anti-human IgG H+L (Amersham) was applied. In one step, human antibody was detected. As a result, H-chain (50 kDa) and L-chain (25 kDa) in human antibody were detected in the transformed cell.

Next, the same transfection experiment was conducted. In addition to the antibody secretion, it is confirmed that the antigen specificity is conserved. Cell culture supernatants were extracted after 24 hours and 48 hours from transfection. Human IgG antibody and anti-GM-CSF specific antibody were detected by ELISA. FIG. 8 illustrates an ELISA result. Purified antibody was diluted in series, and then it was applied as a control for ELISA experiment. pEGFP-transformed cell culture supernatant was applied as a control for transfection experiment as above. Human IgG was recognized in each cell culture supernatant expressing antibody gene transiently. It was confirmed that all of secreted antibodies have specificity against GM-CSF (FIG. 8).

Anti-hGM-CSF antibody or its antigen binding portion obtained as above is able to specifically bind to hGM-CSF causing various diseases, and is able to depress the bioactivity, so that affinity and neutralizing capacity (against hGM-CSF) are shown to be excellent. The anti-hGM-CSF antibody or its antigen binding portion is derived from human monoclonal antibody. Therefore, it does not show immunogenicity or rejection response. The anti-hGM-CSF antibody or its antigen binding portion inhibits the proliferation of dendritic cells. Therefore, it is estimated to make contribution to attenuating antigen-presenting capacity. Considering these properties, the anti-hGM-CSF antibody or its antigen binding portion according to the present invention is effective as a prophylactic and therapeutic agent for diseases caused by hGM-CSF, such as allergic diseases including asthma, atopy and pollinosis; graft rejection, and graft-versus-host disease (GVHD); and autoimmune diseases including rheumatoid arthritis.

What is claimed is:

1. A human monoclonal antibody or its antigen binding portion capable of binding to human granulocyte-macrophage colony stimulating factor (hGM-CSF) and neutralizing bioactivity of the hGM-CSF, wherein the anti-hGM-CSF monoclonal antibody or its antigen binding portion comprises
   (a) a light chain (L chain) complementarity determining region (CDR) 1 domain having the amino acid sequence of SEQ ID NO:5, (b) an L chain CDR 2 domain having the amino acid sequence of SEQ ID NO:6, (c) an L chain CDR 3 domain having the amino sequence of SEQ ID NO:7, (d) a heavy chain (H chain) CDR 1 domain having the amino sequence of SEQ ID NO:8, (e) an H chain CDR 2 domain having the amino acid sequence of SEQ ID NO:9, and (f) an H chain CDR 3 domain having the amino acid sequence of SEQ ID NO:10.

2. The anti-hGM-CSF monoclonal antibody or its antigen binding portion according to claim 1, wherein the anti-hGM-CSF monoclonal antibody or its antigen binding portion has an affinity for hGM-CSF between $2.0\times10^{-10}$ M and $2.3\times10^{-10}$ M.

3. The anti-hGM-CSF monoclonal antibody or its antigen binding portion according to claim 1, wherein approximately 2 μg/mL of the anti-hGM-CSF monoclonal antibody or its antigen binding portion has a neutralizing capacity equivalent to that of a 750- to 1500-fold dilution of blood serum from a patient suffering from idiopathic alveolar proteinosis.

4. The anti-hGM-CSF monoclonal antibody or its antigen binding portion according to claim 1, wherein the anti-hGM-CSF monoclonal antibody or its antigen binding portion inhibits proliferation of a peripheral blood dendritic cell.

5. The anti-hGM-CSF monoclonal antibody or its antigen binding portion according to claim 1, wherein the antibody belongs to $IgG_1$ (κ) class (subclass).

6. A composition comprising:

the anti-hGM-CSF monoclonal antibody or its antigen binding portion according to claim 1, and a pharmaceutically acceptable carrier.

7. The human monoclonal antibody or its antigen binding portion capable of binding to hGM-CSF and neutralizing bioactivity of the hGM-CSF according to claim 1, wherein the anti-hGM-CSF monoclonal antibody or its antigen binding portion comprises a light chain variable region (LCVR) comprising the amino acid sequence of SEQ ID NO:3 and a heavy chain variable region (HCVR) comprising the amino acid sequence of SEQ ID NO:4.

8. The anti-hGM-CSF monoclonal antibody or its antigen binding portion according to claim 7, wherein the anti-hGM-CSF monoclonal antibody or its antigen binding portion has an affinity for hGM-CSF between $2.0\times10^{-10}$ M and $2.3\times10^{-10}$ M.

9. The anti-hGM-CSF monoclonal antibody or its antigen binding portion according to claim 7, wherein approximately 2 μg/mL of the anti-hGM-CSF monoclonal antibody or its antigen binding portion has a neutralizing capacity equivalent to that of a 750- to 1500-fold dilution of blood serum from a patient suffering from idiopathic alveolar proteinosis.

10. The anti-hGM-CSF monoclonal antibody or its antigen binding portion according to claim 7, wherein the anti-hGM-CSF monoclonal antibody or its antigen binding portion inhibits proliferation of a peripheral blood dendritic cell.

11. The anti-hGM-CSF monoclonal antibody or its antigen binding portion according to claim 7, wherein the antibody belongs to $IgG_1$ (κ) class (subclass).

12. A composition comprising:

the anti-hGM-CSF monoclonal antibody or its antigen binding portion according to claim 7, and a pharmaceutically acceptable carrier.

13. The human monoclonal antibody or its antigen binding portion capable of binding to hGM-CSF and neutralizing bioactivity of the hGM-CSF according to claim 1, wherein the anti-hGM-CSF monoclonal antibody comprises an L chain comprising the amino acid sequence of SEQ ID NO:1 and an H chain comprising the amino acid sequence of SEQ ID NO:2.

14. The anti-hGM-CSF monoclonal antibody or its antigen binding portion according to claim 13, wherein the anti-hGM-CSF monoclonal antibody or its antigen binding portion has an affinity for hGM-CSF between $2.0\times10^{-10}$ M and $2.3\times10^{-10}$ M.

15. The anti-hGM-CSF monoclonal antibody or its antigen binding portion according to claim 13, wherein approximately 2 μg/mL of the anti-hGM-CSF monoclonal antibody or its antigen binding portion has a neutralizing capacity equivalent to that of a 750- to 1500-fold dilution of blood serum from a patient suffering from idiopathic alveolar proteinosis.

16. The anti-hGM-CSF monoclonal antibody or its antigen binding portion according to claim 13, wherein the antihGM-CSF monoclonal antibody or its antigen binding portion inhibits proliferation of a peripheral blood dendritic cell.

17. The anti-hGM-CSF monoclonal antibody or its antigen binding portion according to claim 13, wherein the antibody belongs to IgG$_1$ (κ) class (subclass).

18. A composition comprising:
the anti-hGM-CSF monoclonal antibody or its antigen binding portion according to claim 13, and
a pharmaceutically acceptable carrier.

* * * * *

UNITED STATES PATENT AND TRADEMARK OFFICE
CERTIFICATE OF CORRECTION

PATENT NO.         : 7,935,795 B2
APPLICATION NO.    : 12/149009
DATED              : May 3, 2011
INVENTOR(S)        : Kantou Nakajima It is certified that error appears in the above-identified patent and that said Letters Patent is hereby corrected as shown below:

In the Claims:

At column 25, line 33 (claim 1), "amino sequence" should be replaced to read --amino acid sequence--.

At column 25, line 36 (claim 1), "amino sequence" should be replaced to read --amino acid sequence--.

Signed and Sealed this
First Day of September, 2015

Michelle K. Lee
*Director of the United States Patent and Trademark Office*